(12) United States Patent
Kelly et al.

(10) Patent No.: US 9,068,171 B2
(45) Date of Patent: Jun. 30, 2015

(54) METHOD FOR MYCELIATING COFFEE

(71) Applicant: Mycotechnology, Inc., Aurora, CO (US)

(72) Inventors: Brooks John Kelly, Denver, CO (US); James Patrick Langan, Denver, CO (US)

(73) Assignee: Mycotechnology, Inc., Aurora, CO (US)

( * ) Notice: Subject to any disclaimer, the term of this patent is extended or adjusted under 35 U.S.C. 154(b) by 0 days.

(21) Appl. No.: 13/844,685

(22) Filed: Mar. 15, 2013

(65) Prior Publication Data

US 2014/0302560 A1    Oct. 9, 2014

Related U.S. Application Data

(60) Provisional application No. 61/697,506, filed on Sep. 6, 2012.

(51) Int. Cl.
| | | |
|---|---|---|
| A23L 1/29 | (2006.01) | |
| A23L 1/105 | (2006.01) | |
| A23L 1/20 | (2006.01) | |
| C12N 1/14 | (2006.01) | |
| A23F 5/02 | (2006.01) | |
| A23F 5/20 | (2006.01) | |
| A23L 1/28 | (2006.01) | |
| A23L 1/30 | (2006.01) | |
| A23L 1/39 | (2006.01) | |
| A23L 1/08 | (2006.01) | |

(52) U.S. Cl.
CPC ... *C12N 1/14* (2013.01); *A23L 1/28* (2013.01); *A23L 1/3002* (2013.01); *A23L 1/39* (2013.01); *A23F 5/02* (2013.01); *A23F 5/204* (2013.01); *A23L 1/08* (2013.01); *A23L 1/105* (2013.01); *A23L 1/2008* (2013.01)

(58) Field of Classification Search
CPC ........ B32B 9/02; B32B 2262/06; C12N 1/14; A23F 5/145; A23F 5/02; A23F 5/163; A23F 5/204; A23F 5/246; C12R 1/645
See application file for complete search history.

(56) References Cited

U.S. PATENT DOCUMENTS

| | | | |
|---|---|---|---|
| 1,822,227 A | 9/1931 | Lendrich et al. | |
| 2,693,664 A | 8/1949 | Szuecs | |
| 3,749,584 A | 7/1973 | Kurtzman et al. | |
| 4,891,220 A | 1/1990 | Byron | |
| 6,277,396 B1 | 8/2001 | Dente | |
| 6,476,003 B1 | 11/2002 | Jordan et al. | |
| 6,490,824 B1 | 12/2002 | Intabon et al. | |
| 6,558,943 B1 | 5/2003 | Li et al. | |
| 6,569,475 B2 | 5/2003 | Song | |
| 2,419,515 A1 | 8/2011 | Yan et al. | |
| 2002/0137155 A1 | 9/2002 | Wasser et al. | |
| 2004/0009143 A1 | 1/2004 | Golz-Berner et al. | |
| 2004/0211721 A1 | 10/2004 | Stamets | |
| 2005/0180989 A1 | 8/2005 | Matsunaga | |
| 2005/0255126 A1 | 11/2005 | Tsubaki et al. | |
| 2006/0280753 A1 | 12/2006 | McNeary | |
| 2007/0160726 A1 | 7/2007 | Fujii | |
| 2008/0057162 A1* | 3/2008 | Brucker et al. | 426/73 |
| 2008/0107783 A1 | 5/2008 | Anijis et al. | |
| 2008/0171104 A1 | 7/2008 | Zhu | |
| 2008/0193595 A1 | 8/2008 | De Vuyst et al. | |
| 2008/0264858 A1 | 10/2008 | Stamets | |
| 2008/0274234 A1 | 11/2008 | Miller | |
| 2008/0296223 A1* | 12/2008 | Hiromoto | 210/632 |
| 2008/0299645 A1 | 12/2008 | Holliday | |
| 2009/0047236 A1 | 2/2009 | Stamets | |
| 2009/0053363 A1 | 2/2009 | An | |
| 2009/0098244 A1 | 4/2009 | Schatzmayr et al. | |
| 2009/0104310 A1 | 4/2009 | Nakajima | |
| 2009/0130138 A1 | 5/2009 | Stamets | |
| 2009/0220645 A1 | 9/2009 | Martinez | |
| 2009/0280212 A1 | 11/2009 | Sugimoto et al. | |
| 2010/0055241 A1 | 3/2010 | Nakano et al. | |
| 2010/0183765 A1 | 7/2010 | Laan Van Der et al. | |

(Continued)

FOREIGN PATENT DOCUMENTS

| | | |
|---|---|---|
| EP | 1173544 | 1/2002 |
| EP | 2474221 | 2/2011 |

(Continued)

OTHER PUBLICATIONS

MicrobiologyBytes. Introduction to Mycology. Datasheet [online]. Updated Apr. 8, 2009 [retrieved on Feb. 6, 2014]. Retrieved from the Internet: <URL: http://www.microbiologybytes.com/introduction/myc1.html>. specif. p. 8.*

Encyclopedia Britannica. Louis Pasteur. Datasheet [online]. Copyright 2014 Encyclopedia Britannica, Inc. [retrieved on Feb. 6, 2014]. Retrieved from the Internet: <URL: http://www.britannica.com/EBchecked/topic/445964/Louis-Pasteur>. specif. p. 3.*

Russell, R. et al. 2006. Ganoderma—a therapeutic fungal biofactory. Phytochemistry 67:1985-2001. specif. pp. 1985, 1987-1988, 1994-1995, 1997-1998.*

Zhou, X. et al. 2009. *Cordyceps* fungi: natural products, pharmacological functions and developmental products. Journal of Pharmacy and Pharmacology 61:279-291. specif. pp. 279-280.*

(Continued)

*Primary Examiner* — John S Brusca
*Assistant Examiner* — Sharon M Papciak
(74) *Attorney, Agent, or Firm* — Swanson & Bratschun, L.L.C.

(57) ABSTRACT

A method of creating an extract of myceliated agricultural product for human consumption includes providing an agricultural substrate such as rice, where the agricultural substrate has been inoculated by liquid media comprising an aliquot of culture derived from liquid-state fermentation. The culture being selected from the group consisting of Basidiomycota and Ascomycota fungi. Next, the step of enabling mycelium growth on the substrate by controlling temperature, humidity and sterility of the environment. After mycelium growth on the substrate reaches a desired stage, then the step of boiling the substrate in water and separating the water-substrate mixture into aqueous component and non-aqueous components creates an extraction.

11 Claims, 2 Drawing Sheets

(56) References Cited

U.S. PATENT DOCUMENTS

| | | | |
|---|---|---|---|
| 2010/0203189 A1 | 8/2010 | Holliday | |
| 2010/0203194 A1 | 8/2010 | Salminen et al. | |
| 2010/0221385 A1 | 9/2010 | Matsui et al. | |
| 2010/0239711 A1* | 9/2010 | Li et al. | 426/45 |
| 2010/0266726 A1 | 10/2010 | Ogura et al. | |
| 2010/0316763 A1 | 12/2010 | Choi et al. | |
| 2011/0008384 A1 | 1/2011 | Stamets | |
| 2011/0052758 A1 | 3/2011 | Greiner-Stoeffele | |
| 2011/0070332 A1 | 3/2011 | Bernaert et al. | |
| 2011/0081448 A1 | 4/2011 | Dunphy et al. | |
| 2011/0091579 A1 | 4/2011 | Hausman | |
| 2011/0123675 A1 | 5/2011 | Bernaert et al. | |
| 2011/0189220 A1 | 8/2011 | Yang | |
| 2011/0200551 A1 | 8/2011 | Stamets | |
| 2011/0206721 A1 | 8/2011 | Nair | |
| 2011/0229616 A1 | 9/2011 | Anijis et al. | |
| 2011/0262593 A1 | 10/2011 | Binggeli et al. | |
| 2011/0268980 A1* | 11/2011 | Kalisz et al. | 428/532 |
| 2012/0027889 A1 | 2/2012 | Portella | |
| 2012/0034344 A1 | 2/2012 | Menon et al. | |
| 2012/0082754 A1 | 4/2012 | Holliday | |
| 2012/0100249 A1 | 4/2012 | Laan et al. | |
| 2012/0128823 A1 | 5/2012 | Camu | |
| 2012/0171308 A1 | 7/2012 | Da Luz Moreira et al. | |
| 2012/0177781 A1 | 7/2012 | Hayashi | |
| 2012/0231114 A1 | 9/2012 | Chhun et al. | |
| 2012/0244254 A1 | 9/2012 | Takahashi | |
| 2012/0321744 A1 | 12/2012 | Chhun et al. | |
| 2013/0209608 A1 | 8/2013 | Berends et al. | |
| 2013/0209609 A1 | 8/2013 | Moreno et al. | |
| 2013/0337114 A1 | 12/2013 | Sa | |
| 2014/0105928 A1 | 4/2014 | Stamets | |

FOREIGN PATENT DOCUMENTS

| | | | |
|---|---|---|---|
| WO | WO 01/32830 | 5/2001 | |
| WO | WO 2006/107208 | 10/2006 | |
| WO | WO 2011/032244 | 3/2011 | |
| WO | WO 2011032244 A1 * | 3/2011 | A21D 2/08 |
| WO | WO 2011/151831 | 12/2011 | |
| WO | WO 2013/171194 | 11/2013 | |

OTHER PUBLICATIONS

Taylor, J. 2001. Measuring Fungal Growth. Chapter 3.8 In: Microorganisms and Biotechnology, 2$^{nd}$ ed. Thomas Nelson, Ltd. 2001 Delta Place, Cheltenham, U.K. (ISBN 0 17 448255 8). specif. p. 4 (book p. 44).*
MedlinePlus Medical Dictionary. Autoclave. Datasheet [online] Copyright 2014 Merriam-Webster, Inc. [retrieved on Feb. 7, 2014]. Retrieved from the Internet: <URL: http://www.merriam-webster.com/medlineplus/autoclave>.*
English translation.deOliveira, B. et al. WO 2011/032244 A1.Flours produced from fungus myceliated grain.Published Mar. 24, 2011.pp. 1-24. specif. pp. 2, 6-7.*
Liu et al. (2012) Molecules, 17:12575-12586, "Improving the Fermentation Production of the Individual Key Triterpene Ganoderic Acid Me by the Medicinal Fungus *Ganoderma lucidum* in Submerged Culture".
Stamets, Chapter 12, pp. 89-92 "Culturing Mushroom Mycelium on Agar Media."
Zhang et al. (2004) Life Sciences, 75:2911-2919, "Induction of HL-60 apoptosis by ethyl acetate of *Cordyceps sinensis* fungal mycelium."
Autoclave Search (2014) www.meriam-webster.com/medlineplus/autoclave.
Berovic et al. (2003) J. Biotechnol. 103(1): 77-86.
Bok et al. Phytochemistry (1999) 51: 891-898.
"Can You Eat Mycelium?" (2014) wiki.answers.com.
"Eat Mycelium cakes?" (2014) Mycotopia.net.
"Eat Mycelium?" (2014) fungifun.com.
"Eating mycelium to trip" (2014) shroomery.org.
"Eating Mycelium?" (2014) zoklet.net.
"Eating Mycelium" (2014) wisegeek.com Conjecture Corporation.
Firenzuoli et al. (2008) Evid. Based Complement Alternat. Med. 5(1): 3-15.
Foster (2014) "What is Mycelium?" wisegeek.com. Conjecture Corporation.
Han (2005) Solid-state fermentation of cornmeal with the basidiomycete *Ganoderma lucidum* for degrading starch and upgrading nutritional value J. Appl. Micro. 2005, 99: 910-915.
Hashim, Puziah (1997) Effect of Processing on Flavour Precursors, Pyrazines and Flavour Quality of Malaysian Cocoa Beans. PhD thesis, Universiti Pertanian Malaysia.
Ikrawan, Yusep (2003) Influence of Carboxypeptidases on Cocoa Specific Aroma Precursors and Methylpyrazines in Under-Fermented Cocoa Beans. PhD thesis, Universiti Putra Malaysia.
Ishikawa et al. (2001) J. Nat. Prod. 64(7): 932-934.
Kang (2005) Zhongguo Zhong Yao Za Zhi 30(30): 193-195.
Kang (2003) Zhongguo Zhong Yao Za Zhi 28(11): 1038-1040.
Konno et al. (2002) International Journal of Medicinal Mushrooms 4(3): 10-21.
Kuo et al. (1996) Am. J. Chin. Med. (1996) 24: 111-125.
Lakshmi et al. Teratog. Carcinog. Mutagen (2003) 1: 85-97.
Lee et al. (2003) Enzyme and Microbial Technology 32(5): 574-581.
McMahon (2014) "How Can I Make Tempeh?" wisegeek.com Conjecture Corporation.
Mohamed Ali, Aisha Bibi (2010) Production of pyrazine flavours by mycelial fungi. Master's thesis, University of Pretoria.
Morris et al. (2003) Micologia Aplicada Internacional 15(1): 7-13.
Paterson (2006) Phytochemistry 67:1985-2001.
Rodrigues de Melo et al. (2008) Mycoscience 50(1): 78-81.
Shao et al. (2001) Electrophoresis 22(1): 144-150.
Stamets (2003) Chapter 12, pp. 89-92 "Culturing Mushroom Mycelium on Agar Media."
Wasser (2002) Appl Microbiol Biotechnol 60: 258-274.
Willis, W.L. et al. (2010) Effect of Dietary Fungus Myceliated Grain on Broiler Performance and Enteric Colonization with Bifidobacteria and *Salmonella International Journal of Poultry Science.*, 9(1): 48-52.
Wu et al. (2011) Carcinogenesis 32(12): 1890-1896.
Yin et al. (2010) Am. J. Chin. Med. 38(1): 191-204.
Zhang et al. (2010) Journal of Medicinal Plants Research 4(18): 1847-1852.
Zhou et al. (2009) Journal of Pharmacy and Pharmacology 61:279-291.
Encyclopedia Britannica, Louis Pasteur, Datasheet [online]. Copyright 2014 Encyclopedia Britannica Inc. [retrieved on Feb. 6, 2014]. Retrieved from the Internet: <URL: http://www.britannica.com/Ebchecked/topic/445964/Louis-Pasteur>. Specif, p. 3.
English translation. deOliverir, B. et al. WO 2011/032244 A1. Flours produced from fungus myceliated grain. Published Mar. 24, 2011. pp. 1-24. specif, pp. 2, 6-7.
MicrobiologyBytes. Introduction to Mycology. Datasheet [online'. Updated Apr. 8, 2009 [retrieved on Feb. 6, 2014]. Retrieved from the Internet: <URL: http://www.microbiologybytes.com/introduction/myc1.html>. Specif, p. 8.
Paterson, R. et al. 2006. Ganoderma—a therapeutic fungal biofactory. Phytochemistry 67:1985-2001. specif, pp. 1985, 1987-1988, 1994-1995, 1997-1998.
Taylor, J. (2001) "Measuring Fungal Growth." Chapter 3.8 In: Microorganisms and Biotechnology, 2nd ed., Thomas Nelson, Ltd. 2001 Delta Place, Cheltenham, U. K. (ISBN 0 17 448255 8). Specif. p. 4 (book p. 44).
Ulziijargal et al. (2011) : Nutrient Compositions of Culinary-Medicinal Mushroom Fruiting Bodies and Mycelia Int. J. Med. Mushrooms 13(4): 343-349.
Office Action issued Feb. 19, 2014 for U.S. Appl. No. 13/844,685.
International Search Report and the Written Opinion of the International Searching Authority, or the Declaration for PCT/US14/29989 dated Aug. 12, 2014.
International Search Report and the Written Opinion of the International Searching Authority, or the Declaration for PCT/US14/29998 dated Sep. 11, 2014.
Chang et al. (2009) "*Ganoderma lucidum* Extract Promotes Immune Responses in Normal BALB/c Mice In Vivo", in vivo, V. 23: 755-760.

(56) References Cited

OTHER PUBLICATIONS

Sone et al. (1985) "Structures and Antitumor Activities of the Polysaccharides Isolated from Fruiting Body and the Growing Culture of Mycelium of *Ganoderma lucidum*", Agric. Biol. Chem., V. 49(9): 2641-2653.

Zhong et al. (2004) "Submerged Cultivation of Medicinal Mushrooms for Production of Valuable Bioactive Metabolites", Adv Biochem Engin/Biotechnol V. 87: 25-59.

Emden (2015) "Decaffeination 101: Four Ways to Decaffeinate Coffee" Coffee Connection; retrieved from http://www.coffeeconfidential.org/health/decaffeination/ Jan. 29, 2015. 7 pages.

\* cited by examiner

METHOD FOR MYCELIATING COFFEE

CROSS REFERENCE TO RELATED APPLICATION

This application claims priority benefit under 35 U.S.C. §119(e) of U.S. Provisional Application No. 61/697,506, filed on Sep. 6, 2012, entitled "Myceliated Grain and Myceliated Agricultural Materials in Gourmet Human Food Production," the disclosure of which is herein incorporated by reference in its entirety.

FIELD OF THE INVENTION

This invention pertains to methods of liquid-state and solid-state myceliation of agricultural materials into a range of potent nutraceutical and delicious functional foods for humans.

BACKGROUND AND SUMMARY OF THE INVENTION

Tempeh is a soy-based product that typically utilizes *Rhizopus oligosporus* to ferment soybeans. *R. oligosporus* is also used to ferment other legumes.

The present invention utilizes mycelium from select, referenced strains of Basidiomycota and Ascomycota fungi grown in liquid-state culture to solid-state ferment agricultural materials containing or admixed with plant, vegetable and or fungi biomass, so as to directly or indirectly facilitate the production of nutraceuticals and or functional foods specifically intended for human consumption. These protocols are unique in that they employ a zero-waste philosophy in combination with new methods for producing functional foods and nutraceutical formulations which may be used directly, stored for later use, packaged and or shipped.

Mycelium has been used primarily as a source for medicinal extracts and animal food, while the fruiting bodies or mushrooms were used as human food. The novel methodology as disclosed herein exploits mycelial tissue, which can be derived by fermentation of a substrate by a number of gourmet and medicinal fungi, many of which may function interchangeably. A variety of agricultural substrate(s) may be used with the present invention.

Classical fungi produce spore-bearing mushrooms and or vegetative mycelium which contain pharmacologically active metabolites including polysaccharides, glycoproteins, enzymes, triterpenes, phenols and sterols. Mushrooms and mycelium are very similar in that they both produce polysaccharides and metabolites, the ingestion of which induces positive immunomodulation in the human body. However, fruiting mushrooms can be time consuming. This invention quickly produces myceliated gourmet functional foods and nutraceuticals which are protein-rich with taste and texture similar to mushrooms, meat and or meat substitutes, and achieves in these products a wide variety of flavors, colors, smells, and textures. By transforming myceliated grain and myceliated agricultural substrate, novel products are created which provide unique properties similar to mushrooms and or mycelium, including potential as delicious and nutritious meat substitutes.

Metabolites from more than 650 mushroom species are known to have anti-tumor and immunomodulatory effects on humans. Fungi used in this work were chosen because of their unique cell wall polysaccharides and their transformative ability to excrete specific metabolites into substrate to ferment and break it down into smaller molecules for absorption. Most medicinal and or gourmet mushrooms take a long time to come to fruition. In contrast, this invention produces nutraceutical and functional food products that are in some cases more potent than methods utilizing mushroom fruiting bodies.

Fungi are metabolically similar to animals but structurally similar to plants in that they possess a rigid cell wall formed largely of long sugar molecule chains joined by somewhat difficult to digest beta (b-) linkages and to a smaller extent more easily digestible alpha (a-) linkages in conjunction with membrane-bound proteins. In contrast, plant cell walls are made of cellulose polysaccharides whose (1→4) b-glycosidic glucose linkages are likewise difficult to digest by our enzymes; however, as the cell walls of fungi are primarily composed of (1→3) b-glycosidic linkages, with (1→6) linked side chains, they may be broken down by minimal processing using water, heat and mechanical treatment into smaller, more easily digestible, immunologically-active polysaccharide molecules of variable microparticulate size called b-glucans, and related glycoprotein compounds. The immune response to these glucans is dependent upon a- or b-glucan structure, which has primary, secondary, and chiral tertiary structures, explaining the differences in immune response to each fungi's unique a- and or b-glucan profile. Thus, myceliated substrate, with its plethora of unique, immunologically active molecules, is efficiently processed after fermentation into nutraceutical formulations and or compounds and functional foods whose oral activity increases after formulating the extract in association with small molecules in nutraceutical production and in acid hydrolysis (enzymatic digestion) of tempeh-syle myceliated grain substrate. These types of products may attract consumers who wish to derive the general immunomodulating, anti-aging, aphrodisiac, anti-tumor, anti-viral, anti-bacterial, and or anti-fungal properties, activities, and benefits, by orally consuming substrate which has been converted to edible presentations of a- and b-glucans, glycoproteins, proteins, ergosterols, sterols, triterpenes, and fatty acids in the form of nutraceuticals and functional foods.

The invention includes various embodiments including:

A myceliated agricultural product for human consumption including an agricultural substrate such as rice, the agricultural substrate is inoculated by liquid media comprising an aliquot of culture derived from liquid-state fermentation. In one embodiment, the culture is a Basidiomycota fungi, and in another embodiment, the culture is Ascomycota fungi. The liquid-state fermentation yields spherical conglomerations of culture that are sized to interstitially penetrate the substrate to optimize inoculation of the substrate.

The substrate can be any of the enumerated substrates set forth herein, including grain, green coffee beans, green cacao beans, green vanilla beans, various seeds, rice, and non-legume beans.

The spherical conglomerations are sized smaller than 2 millimeters in one embodiment, which allow for and enable growth of hyphae in three dimensions about the spherical conglomerations. This accelerates the myceliation process.

In another embodiment, when stirred or otherwise agitated, the hyphae are sheared due to the agitation of the liquid media to limit the size of the conglomerations to between 10 microns to 1 millimeter in diameter.

The substrate can be pasteurized or sterilized, depending on the substrate.

In one embodiment, the liquid media is stationary, and the liquid-state fermentation is performed in an undisturbed environment, which is semi-anaerobic utilizing the Pasteur effect to greatly enhance and direct mycelial growth downward from a floating mass into the stationary liquid media.

In an alternate embodiment, the liquid media is continuously swirled during liquid-state fermentation and sterile air is injected to deliver oxygen to the liquid media.

In yet another embodiment, the liquid media is housed in a tank, and portions of the liquid media are selectively removed and replaced by new media, which is sterile, to enable continuous harvest of liquid media. This enhances production efficiency.

Various health benefits of the present invention are apparent, and in one embodiment, the myceliated agricultural product for human consumption is intended to effectuate neuro-regeneration and neuro-protection in humans. In this embodiment the agricultural substrate has substrate elements defining interstitial spaces there between, such as rice. The substrate is at least partially coated with a mixture of vegetable oil and lecithin. The vegetable oil increases the interstitial space between substrate elements to improve myceliation and the lecithin enhances neuro-protective effects of the product. The culture is selected from the group consisting of: *Hericium erinaceus* and *Tremella fuciformis*, which have proven neuro-regeneration properties in humans. It is noteworthy that the mycelium of *Hericium erinaceus* has been indicated to include components that improve neuroregeneration effects over the components found in the fruiting body of the *Hericium erinaceus*.

Preferably the vegetable oil is olive oil, which may have neuro-protectant properties.

DETAILED DESCRIPTION

Figure 1:
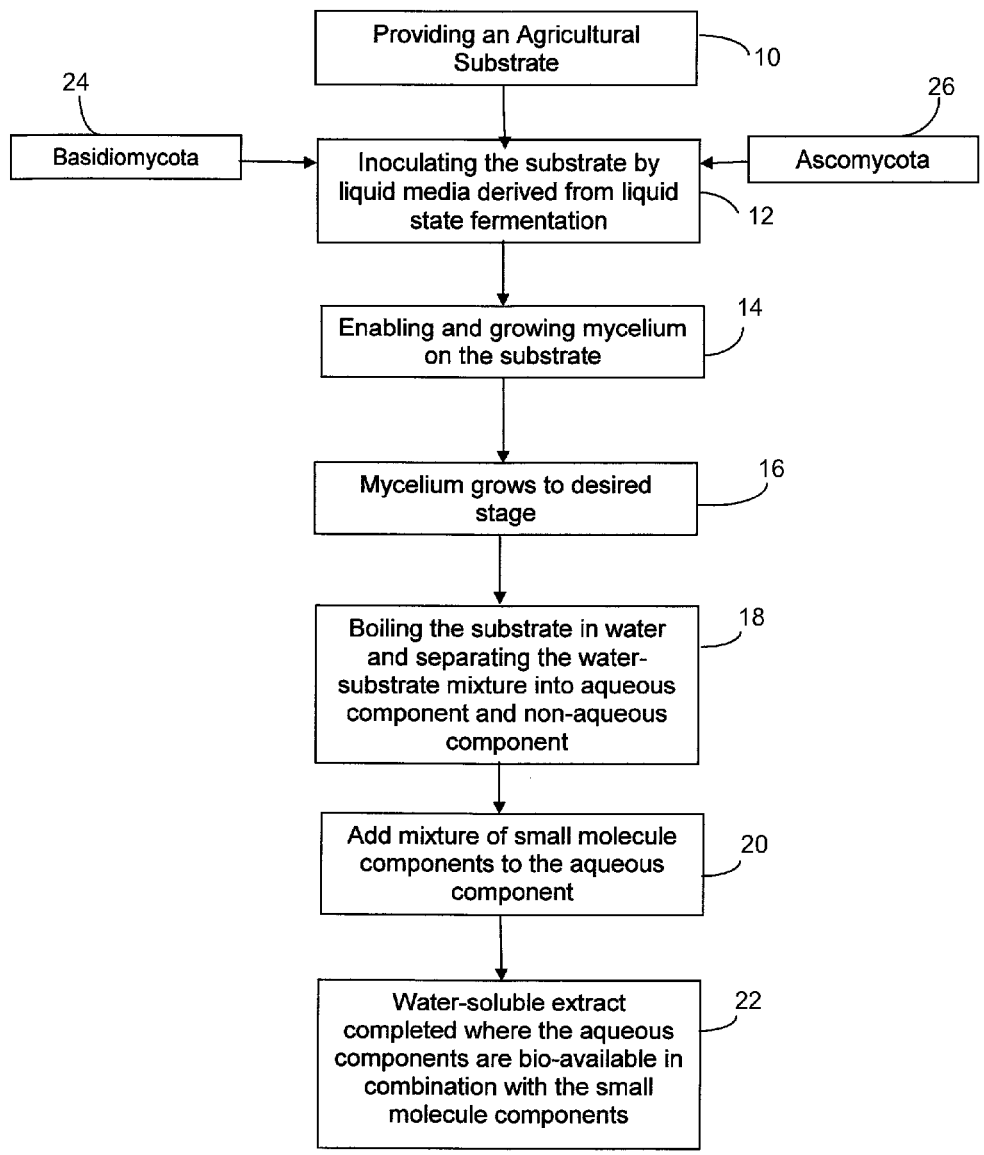
FIG. 1 is a flow chart of a method of creating a bio-available mycelium extract in accordance with the present invention.

FIG. 1 shows a flow chart of a method of creating an extract of myceliated agricultural product for human consumption. The step 10 provides an agricultural substrate, the step 12 inoculates the substrate by liquid media comprising an aliquot of culture derived from liquid-state fermentation, the step 14 enables mycelium growth and the step 16 grows mycelium on the substrate, the step 18 includes boiling the substrate in water and separating the water-substrate mixture into aqueous and non-aqueous components after mycelium growth on the substrate reaches a desired stage, the step 20 adds a mixture of small molecule components to the aqueous components whereby the aqueous components mix in bio-available combination with the small molecule components to facilitate water solubility of the extract.

In one embodiment, the step 24 utilizes a culture of Basidiomycota fungi to enable step 12. In an alternate embodiment, the step 26 utilizes and Ascomycota fungi to enable step 12.

Figure 2:
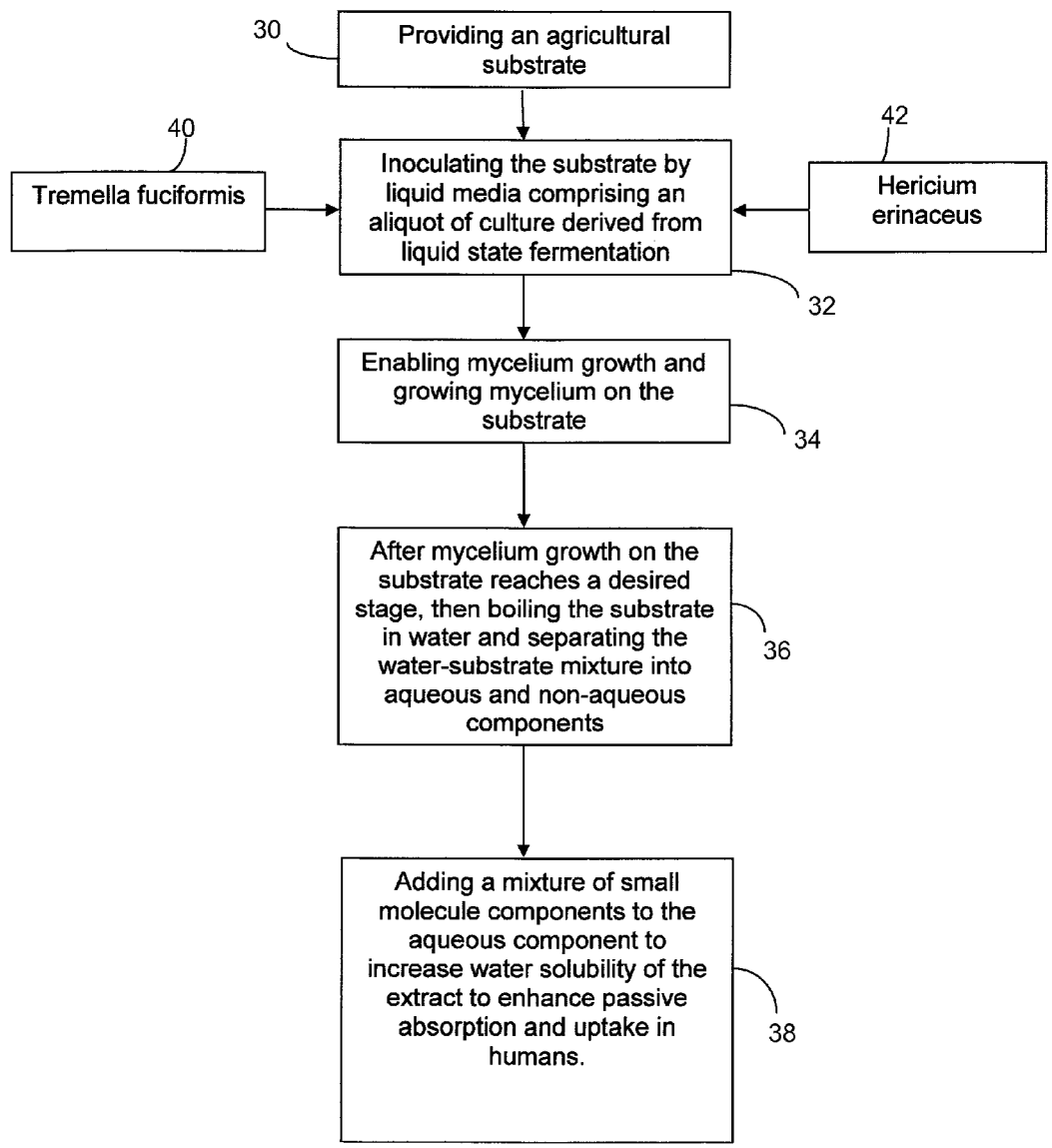
FIG. 2 is a flow chart of a method of creating an extract of myceliated agricultural product for human consumption to effectuate neuro-regeneration and neuro-protection in humans in accordance with the present invention.

FIG. 2 shows a method of creating an extract of myceliated agricultural product for human consumption to effectuate neuroregeneration and neuro-protection in humans in accordance with the present invention.

The method includes the step 30 of providing an agricultural substrate, the step 32 of inoculating the substrate by liquid media comprising an aliquot of culture derived from liquid-state fermentation, the step 34 of enabling mycelium growth and growing mycelium on the substrate, the step 36 of boiling the substrate in water and separating the water-substrate mixture into aqueous and non-aqueous components. Step 36 occurs after mycelium growth on the substrate reaches a desired stage. The step 38 adds a mixture of small molecule components to the aqueous components to increase water solubility of the extract to enhance passive absorption and uptake in humans.

The step 32 of inoculating includes the step 40 of inoculating with *Tremella fuciformis*. In an alternate embodiment, the step 32 of inoculating includes the step 44 of inoculating with *Hericium erinaceus*.

The step 34 of enabling and growing mycelium on the substrate includes regulating temperature and humidity in a sterile environment. The mycelium then grows automatically. Ideally the mycelium is grown in a container that allows only a small amount of sterile air to enter the container. Volumes of sterile air are regulated by capping the container. This modulates ambient oxygen in the container.

The step 34 grows the mycelium to a desired stage, for example, where fruiting bodies begin to appear on the surface of the substrate.

The step 36 boils the substrate in water to separate the polysaccharides in the mycelium and other beneficial components to suspend in the water, separating aqueous component from the residual substrate solids. The non-aqueous component includes the substrate solids. Separating the aqueous component from the non-aqueous component can be accomplished by filtering or siphoning. It can be appreciated that other methods known in the art can be utilized.

The step 38 adds a mixture of small molecule components to the aqueous component. This enables the aqueous components to be more bio-available in vivo. It also enables passive absorption of the aqueous components through the lining of the mouth, esophagus, stomach, and lining of the upper portions of the small intestine. Active absorption occurs for any remaining aqueous components at the distal end of the small intestine.

Fungi Strains

Specific fungi strain selection and the growing of strains organically is important for maximizing production of immunologically active-polysaccharides and metabolites from agricultural substrate(s). Agricultural substrates are dichotomized as those which require sterilization before inoculation such as rice, cereal grains, and seeds, and those which require pasteurization before inoculation, such as spices, dried fruits and vegetables, tea mixes, green vanilla beans, green cacao beans, and green coffee beans. In the second category, pasteurization is sufficient, as sterilization destroys or indelibly alters these substrates.

*Agaricus blazei* is referenced to produce unique a- and b-glucans called glucomannan and riboglucan, which are anti-viral, into substrate. *A. blazei* polysaccharide extracts have been shown to be anti-cancer and co-therapeutic with other mycelial extract of fungi listed in this invention. Methods to optimize biomass and extracellular polysaccharide production have been reported.

*Cordyceps sinensis* produces Cordycepic acid, Adenosine, D-Mannitol, and Cordycepinadenosine which are immunomodulating and anti-viral. *C. Sinensis* extracts have been shown to be anti-aging and aphrodisiacal. Mycelial sterols isolated from *C. sinensis* have been shown to inhibit the proliferation of numerous cancer cell lines. *C. sinensis* mycelial polysaccharide extracts have been shown to induce hypoglycemia.

*Flammulina velutipes* mycelium has been shown to have a polysaccharide profile that is immunomodulating. *F. velutipes* mycelium composes a unique ergosterol and amino acid profile, sterpuric acid, mannitol, ribitol, and the nucleosides guanosine and adenosine. Enokipodins A-D extracted from *F. velutipes* mycelium are broad spectrum anti-microbial terpenes. The proteins flammulin and velutin exhibit anti-HIV and anti-HPV activity.

*Ganoderma lucidum*'s polysaccharide profile has been shown to be immunomodulating in human cell lines and also in clinical studies. *G. lucidum* mycelial extracts have anti-peroxidative, anti-inflammatory, and anti-mutagenic properties. *G. lucidum* extracts have been shown to be anti-aging and aphrodisiacal. The triterpenoid profile of *G. lucidum* has been determined and shown to be anti-hepatotoxic and hepatoprotective, anti-tumor, anti-angiogenic, anti-hypertensive, hypocholesterolemic, anti-histaminic, and anti-HIV. *G. lucidum*, in addition to producing polysaccharides and glycoproteins, likewise produce triterpenes, such as ganoderic and lucidenic acids, phenolic compounds, and sterols which also have high biological activity and therapeutic properties and are in themselves anti-oxidant, anti-tumor, anti-bacterial, anti-cancer, anti-inflammatory, anti-histamine, hypotensive, sedative, and meditative after oral consumption.

*Grifola frondosa*'s polysaccharide profile has been shown to be immunomodulating and anti-oxidative. *G. frondosa* produces ergosterols and an anti-oxidative profile of fatty acids. The anti-tumor effects of *G. frondosa* extracts on in vitro cancer cell lines have been investigated, and shows promise for diabetes patients as being hypoglycemic.

*Hericium erinaceus* mycelial and fruiting body extracts have been shown to be anti-mutagenic and immunomodulatory across various cell lines. *H. erinaceus* uniquely produces hericenones in fruit bodies and erinacines in mycelium, structurally determined compounds that can pass the blood-brain barrier and promote secretion of Nerve Growth Factor (NGF) in certain regions of the brain. Erinacenes have been shown to be greater potentiators of NGF expression than hericenones.

Aspects of *Lentinula edodes*' polysaccharide profile has been determined and shown to be immunomodulating and anti-viral. Lentinan and other metabolites have been studied for their numerous health care benefits. In some countries, lentinan is classified as an anti-neoplastic polysaccharide and is available for clinical use. Addition of lentinan to standard cancer therapies has been shown to result in increased tumor necrosis and with hepatocellular carcinoma and improved quality of life in patients with esophageal carcinoma.

*Phellenis linteus* extracts have been shown to exhibit anti-tumor activity.

*Polyporus umbellatus* polysaccharide extracts have been studied and shown to be anti-cancer, immunomodulating, anti-malarial, and hepatoprotective.

*Inonotus obliquus* mycelial polysaccharide extract has demonstrated anti-tumor, hypoglycemic, and anti-oxidative properties.

*Pleurotus ostreatus* mycelium and fruit body composition have been shown to be very similar, differing only in amino acid content. The mycelial polysaccharide profile consists primarily of laminarin, the extract of which has been shown to be immunomodulating. Lovastatin, isolated from the mycelial broth of *P. ostreatus*, exhibits anti-carcinoma activity, inhibits growth of bacteria and fungi, and lowers cholesterol.

*Trametes versicolor* produces heteroglucans with a-(1→4) and b-(1→3) glycosidic linkages with fucose in PSK (Krestin) and rhamnose and arabinose in PSP, have been shown to be anti-tumor and immunomodulatory. PSK, an approved drug paid for by national health care in Japan, is a mycelial extract which exhibits immunomodulating, anti-viral, and cholesterol regulating properties.

Mycelial polysaccharide extracts of *Tremella fuciformis* have been shown to be therapeutic for various circulatory disorders, to be neurologically healthy, anti-carcinoma, anti-tumor, and anti-aging.

Fungi strains used herein also make proteins, enzymes, triterpenes, and sterols from substrate which have potent biological activity. *G. lucidum* produces a protein called LZ-8 which has immune modulating and anti-tumor properties.

Liquid-State Fermentation

In this invention, liquid-state fermentation is used in specialized relation with solid-state production of myceliated grain suitable for presentation in the ancient tempeh form, or in more contemporary forms of functional foods such as filets, burgers, patties, sausages, or as precursor for subsequent production of nutraceutical formulations by further processing to create products with health care benefits far beyond those of the original substrate. In related fashion, after solid-state fermentation of coffee beans, vanilla beans, or cacao beans, this invention relies on traditional baking, toasting, or roasting myceliated beans as per conventional preparation methods in order to utilize and enjoy health care benefits beyond those of the original substrate. Protocols employing liquid-state and solid-state fermentation of fungi are important, as strains utilized in this work are facultative aerobes that consume glucose at a greater rate when subjected to a semi-anaerobic environment.

Pharmacological Compounds

Mushroom and mycelium extracts have been shown to contain a variety of pharmacologically important compounds. The pharmacological activity of these compounds depends on their molecular structure in solution. Utilization of conventional pharmacological techniques of crystallizing or otherwise solidifying compounds of interest for delivery in pill form may diminish or destroy the effectiveness of the compounds by altering the macromolecular structure, generally done in other art by chemically modifying polysaccharide structure, for example by way of Smith degradation, formolysis, and carboxymethylation, chemical engineers have increased polysaccharide water solubility thereby improving anti-cancer activity. In order to present mycelia extract to the human body fit for oral ingestion in a water-soluble, unaltered form, these structures must remain in solution in association with small molecules.

Small Molecule Association for Improved Bioavailability

Small molecule association and improved bioavailability is achieved by formulated association of concentrated mycelial extracts containing polysaccharides, glycoproteins, proteins and enzymes, triterpenes, sterols, ergosterols, fatty acids, and other metabolites and with or without the small molecules water, ethyl alcohol, citric and ascorbic acid, essential oils of grapefruit, orange, lemon, lime, and tangerine, evaporated cane sugar, and honey, promotes and accentuates passive absorption of mycelial extract after oral consumption.

Oral Delivery

The novel delivery method presented herein may be preferable to consumers of nutraceuticals and functional foods. Consumer medications and supplements are often required to be taken as pills or injections on a routine basis. This necessity causes discomfort and or annoyance on a general level, and may cause patient noncompliance. Nutraceuticals such as the honey formulations, and functional foods such as the tempeh-style myceliated grain, egg noodles from myceliated flour, libations brewed from myceliated coffee beans, and chocolate or vanilla confections and powders made from myceliated green cacao or myceliated green vanilla beans may provide a more pleasing delivery system than other related art.

Consumers are concerned about the glycemic index of foods, as chronically high blood sugar leads to many health complications, such as diabetes, and accelerates aging. Certain strains, such as *Cordyceps sinensis* and *Ganoderma lucidum*, contain polysaccharides that are hypoglycemic. After fermentation and processing, tempeh-style products made from rice have a higher percentage of protein and a lower percentage of carbohydrate than original substrate. The present invention does not utilize or require common anti-caking agents such as gypsum which are not suitable or desirable in human food. Instead, anti-caking agents such as 1 mL to 10 mL olive oil containing 1% to 10% (w/v) dissolved lecithin, per 1 lb to 4 lb of brown rice, grains, and seed is used to reduce the glycemic index of these tempeh-style products, increase interstitial space in substrate for more efficient floating and submerged liquid-state culture inoculation, and to provide extra nutrition to the fungi.

Key aspects of this invention are that the aforementioned fungi are scientifically-referenced as gourmet and or medicinal, are known to taste delicious, and are well recognized commercially. Methods herein differ from those of related applications in employing more efficient inoculation and fermentation technologies that optimize utilization of interstitial space in and between items of substrate. By promoting swift and thorough inoculation of substrate, novel tempeh-like products suitable for cooking and subsequent human consumption are formed. Other art produces myceliated grains for flour, but does not utilize the art disclosed herein for efficient inoculation, solid-state fermentation, and presentation for consumption in the tempeh-form as processed into breads or egg noodles.

Coffee

It has been shown that some fungi degrade caffeine. Coffee brewed from roasted myceliated green coffee beans lack compounds that make coffee bitter, and subsequently make a smooth drink lower in caffeine content than unmyceliated substrate. This invention also improves upon prior art by pasteurizing green coffee beans before liquid tissue inoculation instead of using them raw or sterilizing them. Using liquid-state and solid-state fermentation techniques as disclosed herein, pharmacologically active compounds from *Agaricus blazei, Cordyceps sinensis, Ganoderma lucidum, Hericium erinaceus, Grifola frondosa, Pleurotus eryngii, P. ostreatus, P. citrinopileatus, P. djamor, Trametes versicolor, Lentinula edodes, Flammulina velutipes, Volvariella volvacea, Hypsizygus marmoreus, Pholiota nameko, Tuber melanosporum, Lentinus edodes, Morchella hortensis, Polyporus umbellatus*, and *Tremella fuciformis* are made bioavailable by toasting or roasting agricultural substrate composed of myceliated green coffee beans.

Extracts

Extractions of mycelial concentrates from agricultural substrate and their subsequent associations with small molecules in honey creates a novel, water-soluble delivery system for delivering pharmacologically active compounds which are quickly metabolized. Oral consumption of formulated polysaccharide extracts in association with small molecules such as water, citric acid, ascorbic acid, citrus essential oils, and honey, greatly enhances passive metabolic and digestive uptake from the mouth through the small intestine, resulting in enhanced absorption and utilization of pharmacologically active compounds and derivations thereof.

This invention is also a method wherein agricultural substrate myceliated with *Agaricus blazei, Cordyceps sinensis, Ganoderma lucidum, Hericium erinaceus, Grifola frondosa, Pleurotus eryngii, P. ostreatus, P. citrinopileatus, P. djamor, Trametes versicolor, Lentinula edodes, Flammulina velutipes, Volvariella volvacea, Hypsizygus marmoreus, Pholiota nameko, Tuber melanosporum, Lentinus edodes, Morchella hortensis, Polyporus umbellatus*, or *Tremella fuciformis*, is deep-frozen for later use after fermentation in either small-scale or large-scale solid-state production, wherein the fermented product is then cooked, fried, boiled, mashed, pressed, baked, toasted, roasted, and or blanched in aqueous and or oil-based solution after completion of fermentation. Products may be used directly, and or reformulated into value-added nutraceuticals and delicious functional foods. Products are packaged into tempeh-form meat substitutes such as sausages, burger patties, filets, ground meat, jerky, egg noodles, and sauces. Coffee brewed from roasted myceliated green coffee bean substrate lacks compounds that make regular coffee bitter, and subsequently makes a smooth drink lower in caffeine content than that brewed from unmyceliated green coffee beans, resulting in both a nutraceutical and a functional food. This method is also used to ferment herbs such as comfrey, calendula, chickweed, plantain, lavender, goldenseal, for oral, topical and or other nutraceutical and functional food application to increase potency in downstream formulations such as value-added soaps, salves, and syrups. This invention is also a method for using *Ganoderma lucidum, Pleurotus* and or *Cordyceps sinensis* to produce myceliated grain and or other myceliated materials, and as a potency, flavor, texture, smell and color enhancer in the production of nutraceutical formulations and functional foods. *C. sinensis* grown on grain may be cooked as stuffing into turkeys, ducks, or chickens. This invention describes a method for producing "Truffle-Oil", oil-based extracts of truffle cultures useful for salad dressings, gourmet cooking and food processing. These products may attract consumers who wish to derive the general immunomodulating, anti-aging, aphrodisiac, anti-tumor, anti-viral, anti-bacterial, and or anti-fungal properties, activities, and benefits, by orally consuming substrate which has been converted to edible presentations of a- and b-glucans, glycoproteins, proteins, ergosterols, sterols, triterpenes, and fatty acids in the form of nutraceuticals and functional foods.

Hyphael Spheres

This invention employs agitation techniques to produce hyphael spheres 10 µm to 10 mm in diameter, the use of which greatly increase the inoculation efficiency of solid-state fermentation because spheres grow in all directions. Liquid-state fermentation agitation and swirling techniques include: mechanical shearing using magnetic stir bars, stainless steel impellers, injection of sterile high-pressure ambient air, injection at high-pressure of sterile media, and or the use of shaker tables. Higher agitation and swirling rates, in conjunction with air and media injections, produce smaller mycelial spheres, aliquots of which are used to inoculate solid-state agricultural substrate(s) for subsequent semi-anaerobic fermentation.

Process Example #1

Using specific and pure strains of Fungi obtained from referenced collections are manipulated in sterile environments at 68 degrees F. to 90 degrees F., in 1 gal to 10 gal plastic bags, 1 qt to 1 gal glass jar, or on 10 cm to 15 cm Petri plates, using undefined, organic fruit and vegetable-based media with 1.5% agar (w/v), in order to monitor and ensure the general vigor and health of strains. Mycelial samples are grown in a gentle, ambient sterile airflow for 2 to 4 weeks, then excised from Petri plates and subsequently used for inoculation into liquid-state fermentation employing a similar undefined fruit and vegetable-based media (but with no agar), using ambient air, in 1 qt to 1 gal glass jars, with agitated or unagitated cultures in ambient air in stainless steel tanks which have been designed for commercial beer brewing and/or fermentation. There is a subtle difference between unagitated and agitated liquid-state fermentation. Unagitated liquid-state fermentation forms a floating mass of hyphae which exhibits continuous growth at interface of liquid and air. The mycelium of agitatated and or swirling cultures grows very quickly as hyphael spheres, which being hydrated, remain submerged, and have the appearance of gelatinous beads in small diameter. Hydrated hyphael spheres collapse upon desiccation, making them useful in inoculating petri-plates for strain propagation and quality control. Sphere diameter in liquid-state fermentation is inversely proportional to agitation intensity and volume. Hyphael shear becomes more efficient at higher agitation and swirling intensity, and once sheared, hyphae form new spheres of smallest possible diameter, growing in size until they shear again. When employed in continuous liquid-state fermentation, there exists a constant ratio of sphere diameters, and therefore a constant supply of spheres on the order of microns. Thus, mycelial sphere diameter is manipulated for more efficient inoculation with inoculation efficiency being inversely proportional to sphere diameter.

Process Example #2

In using unagitated liquid-state fermentation, after commanding the liquid-state medium for a growth period of 2 to 4 weeks, cultures form a floating mass of hyphae, which are gently blended with a sharp, sterile cutting device prior to being used for inoculation. Gentle blending is achieved by mixing or low homogenization in a commercial blender in short bursts at slow speeds. Aliquots of blended liquid-state culture are used to inoculate sterilized unprocessed fruits and or vegetables, cereal grains, and/or culinary seed, or pasteurized culinary spice, medicinal herbs, natural flavorings, tea mixes, green vanilla beans, green cacao beans, and/or green coffee beans.
Substrate Treatment Agricultural substrate requiring sterilization such as unprocessed fruits and/or vegetables, cereal grains or culinary seed, is modified using heat treatment by pressure cooking for 90 minutes at 15 lb/in$^2$ and then cooled to room temperature prior to inoculation by liquid-state culture(s). In related fashion, agricultural substrate not able to withstand extremes of sterilization as above, such as most culinary spice, medicinal herbs, natural flavorings, tea mixes, green vanilla beans, green cacao beans, and/or green coffee beans must first be pasteurized. This method calls for incubation of fungi in solid-state fermentation performed at a temperature range of 30° C.-37° C., for up to 60 days prior to processing and or harvest. Pasteurization of agricultural substrate is achieved by placement into 1 qt to 1 gal glass jars, or as 1 lb to 8 lb aliquots in plastic growth bags made for growing fungi with an appropriate breather patch, and subjecting the agricultural substrate to dry heat treatment for 30 min to 90 minutes in covered stainless steel trays using ambient air heated at 145 degrees F. to 195 degrees F. Pasteurized agricultural substrates are cooled to room temperature and inoculated using 0.1 mL to 10 L aliquots of liquid-state fermentation culture. Inoculations into liquid-state and solid-state substrate(s) for fermentation are performed with blended unagitated liquid-state culture or micron-sized spheres from agitated liquid-state culture.

Process Example #3

In one embodiment: small batch liquid-state and solid-state fermentation; pure cultures of fungi are grown semi-aerobically and inoculated into 1 qt to 1 gal glass jars, or into 1 gal to 5 gal autoclavable plastic bags containing properly prepared grain or similar agricultural materials such as fruit, vegetables, herbs, spices, teas, green vanilla beans, green cacao beans, and/or green coffee beans; then, depending upon strain of fungi and substrate, grown at 70 degrees F. to 90 degrees F. Cultures in jars or bags are gently mixed every few days until they command the substrate whereby eventually becoming somewhat resistant to mixing or shaking, usually 2 to 4 weeks depending upon strain, and are intended for small-scale production of functional food products sold in a tempeh form. The myceliated green vanilla beans are cooked or baked; the myceliated green cacao beans are baked or toasted; and the myceliated green coffee beans are toasted or roasted. Myceliated grain presented in tempeh form, or as an ingredient in food(s) including soups, stir fries, breads, and meat-substitutes, is made safe to eat, and bio-available, by cooking on low to medium heat, 145 degrees F. to 165 degrees F., for 10 min to 60 min, at some point prior to consumption. Other cultures in jars or bags, such as herbs and spices can be dried at 100 degrees F. to 145 degrees F. for 1 h to 24 h, packaged and used conventionally to enjoy the benefits of this invention.

Process Example #4

Decreasing Ribonucleic Acid Levels in Substrate

This invention is also a method for decreasing Ribonucleic Acid (RNA) levels in fully-myceliated agricultural substrate(s) from *Agaricus blazei, Cordyceps sinensis, Ganoderma lucidum, Hericium erinaceus, Grifola frondosa, Pleurotus eryngii, P. ostreatus, P. citrinopileatus, P. djamor, Trametes versicolor, Lentinula edodes, Flammulina velutipes, Volvariella volvacea, Hypsizygus marmoreus, Pholiota nameko, Tuber melanosporum, Morchella hortensis, Polyporus umbellatus,* or *Tremella fuciformis.*

To decrease RNA levels, 1 h to 24 h before harvest, myceliated substrate is heat-treated from 1 min to 2 h at 145 degrees F. to 195 degrees F., allowed to recover from 45 min to 48 h, then harvested and processed into nutriceutical formulations and gourmet functional food. This invention also uses golden strains of *Morchella* which ferment the agricultural substrate analogous to the taste, smell, flavor and texture of honey, producing an effective substitute for sugar in some recipes. This invention is also a method for using Matsutake mycelium to produce stand alone myceliated grain and or other myceliated materials, as a potency, flavor, texture, smell and color enhancer analogous to the spice cinnamon (*Cinnamomum zeylanicum*). For making delicious fish-meat substitutes using *Heracium erinaceus.* This invention is also a method using *H. erinaceus* and strains of *Pleurotus* to produce fish-meat analogues of similar texture, taste and flavor to crab, lobster, and fish, both freshwater and saltwater. These products may attract consumers who wish to avoid gout and or to derive the general immunomodulating, anti-tumor, aphrodisiac, anti-tumour, anti-viral, anti-bacterial, and or anti-fungal properties, activities, and benefits, by orally consuming substrate which has been converted to edible presentations of a- and b-glucans, glycoproteins, proteins, ergosterols, sterols, triterpenes, and fatty acids in the form of nutriceuticals and functional foods.

Recipe Examples Utilizing Myceliated Substrates

Recipe Example #1

Garlic buttered myceliated rice, myceliated grain or myceliated seed. Yield: 2 servings. Prep to serving time 20 min.

Ingredients: 2 large finely chopped shallots or purple onions; 20 cloves garlic finely chopped; 1 lb myceliated rice, myceliated grain or myceliated seed; 4 tsp olive oil; 4 tsp butter; 1 tsp salt; ½ tsp pepper. Preparation: warm a large frying pan over medium-high heat. Add the oil and swirl around, add salt and butter, when butter melts add pepper and then the myceliated rice, myceliated grain or myceliated seed and ¼ cup of water. Prep may be embellished with any vegetable of choice. Simmer, stifling, with lid off until the ¼ cup of added water is quickly evaporated, 5 to 10 min. Cool and serve in a new form of functional food the inventors define herein as "Boulder Tempeh" and "Mushroom Rice".

Recipe Example #2

Vegetable Stir Fry with myceliated rice, myceliated grain or myceliated seed. Yield: 4-6 servings. Prep to serving time 30 min. Ingredients: ¼ cup finely chopped shallots or purple onion; 5-6 cloves garlic finely chopped; 1-2 thumb-size pieces galangal OR ginger, sliced into thin matchstick pieces; ½ to 1 small fresh red chili, sliced, OR ¼ to ½ tsp chili flakes; 1 medium-size carrot, sliced; 1 lb myceliated rice, myceliated grain or myceliated seed; 1 small head cauliflower, cut into florets; 1 small head broccoli, cut into florets; 1 red pepper, sliced into strips; 2-3 cups baby bok choy, or other Chinese cabbage (leaves left whole if not too large, otherwise cut in half or thirds); handful fresh That basil; 2 Tbsp coconut oil or other vegetable oil. Stir Fry Sauce: ⅔ cup coconut milk; 2+½ Tbsp fish sauce (vegetarians/vegans: substitute in 2 Tbsp soy sauce plus 3 Tbsp fresh lemon juice with 1 avocado); 3+½ Tbsp fresh lime juice; 1+½ Tbsp soy sauce; ⅓ to ½ tsp dried crushed chili (chili flakes); 2+½ tsp brown sugar. Preparation: combine all 'stir fry sauce' ingredients together in a cup or bowl except myceliated rice, myceliated grain or myceliated seed. Stir well to dissolve the sugar. Taste-test the sauce, keeping in mind that the first taste should be spicy-salty, followed by sweetness and the rich taste of the coconut milk. Adjust these flavors to suit your taste, adding more lime juice if too sweet or salty (note that it will be less salty when combined with the vegetables). Warm a wok or large frying pan over medium-high heat. Add the oil and swirl around, then add the shallot/onion, garlic, ginger, and chili. Stir-fry 1-2 minutes, then add the carrot, mushrooms, and cauliflower (if using). Also add ¼ of the stirfry sauce. Continue stir-frying 2-3 minutes and add myceliated rice, myceliated grain or myceliated seed. Add the broccoli and red pepper plus up to ½ of remaining stir-fry sauce, enough to gently simmer vegetables in the sauce (5 minutes). Note: this is a 'saucy' stir-fry that is never dry—the sauce is meant to enhance the flavor the myceliated rice, myceliated grain or myceliated seed it is served with. Finally add the bok choy or Chinese cabbage. Add more of the stir-fry sauce as needed, enough to just cover vegetables in sauce. Simmer until bok choy or cabbage is cooked but still bright green with some crispness (2-3 minutes more). Remove from heat and do one last taste-test. If not salty enough, add a little more fish or soy sauce. If too salty or sweet, add another squeeze of lime juice. Add more salt, sugar or chili if desired. Top with fresh basil, cool and serve in a new form of vegetable stir fry the inventors define herein as "Boulder Tempeh Vegetable Stir Fry".

Recipe Example #3

Chicken Soup with myceliated rice, myceliated grain or myceliated seed. Yield: 10 servings. Cooking to serving time: 4 h and 30 min. Ingredients: 1 (5-pound) roasting chicken, duck or goose; 3 large yellow onions peeled and chopped; 4 cups ¼-inch-diced carrots, unpeeled and chopped; 1 lb spinach; 4 large potatoes unpeeled and chopped; 4 cups ¼-inch-diced celery; ½ lb broccoli chopped, ¼ cup minced fresh parsley; 15 sprigs fresh thyme; ¼ cup minced fresh dill; 10 heads of garlic peeled and cut in half crosswise; 2 tablespoons salt; 2 teaspoons ground whole black peppercorns; 4 Poblano Peppers; 4 Anaheim Peppers; 4 of Any Pepper Combination; 1 lb myceliated rice, myceliated grain and or myceliated seed. Directions: Place the chicken in a 16- to 20-quart stainless steel kettle. Add 8 quarts of water and bring to a boil. Simmer the chicken by itself, covered by water, with a lid on the metal kettle, for 3 hours on medium to high with boiling. Add water to retain water level. Remove from heat and allow chicken to cool enough to debone, then remove meat from bone (discarding bone and skin). Add the deboned meat back to the pot and continue simmering, and add the rest of the ingredients including onions, carrots, celery, parsnips, parsley, thyme, dill, garlic, seasonings peppers and myceliated rice, myceliated grain, and or myceliated rice. Cook for 1 h. Cool 30 min and enjoy Chicken Soup in a new form the inventors define herein as "Boulder Tempeh Chicken Soup".

Recipe Example #4

Spinach Curry, or Saag, with myceliated rice, myceliated grain or myceliated seed. Saag is a type of Indian curry featuring cooked spinach, onions and garlic. There are many versions, and almost any vegetable and or grain can be included that which is myceliated. This recipe is totally vegan, and is somewhat spicy and features carrots, coconut milk, spinach, myceliated rice, myceliated grain, myceliated seed. Garam Masala is a spice blend and is generally very tasty but not spicy hot. Omit or reduce the jalapeno and garam masala if you are sensitive to spice. Yield: 4 servings. Cooking to serving time 1 h. Ingredients: 1 lb myceliated rice, myceliated grain and or myceliated seed; two blocks of frozen spinach; one large onion; four carrots; one jalapeno; 7 cloves garlic; cooking oil (olive, coconut or ghee); 1 can coconut milk; the juice of a lemon; 1 tbsp garam masala. What to do: set the blocks of spinach in a pot of hot water on low heat to thaw. Dice the onion and carrots, mince the garlic and jalapeno. Set a large wok or skillet on medium and add the oil and the garam masala. Use enough oil to absorb the spices and still be fluid across the bottom of the pan (about 3 tbsp). After about two minutes when the oil is hot, add the garlic and jalapeno. After cooking just a minute, add the onion and carrots. Cover and reduce heat to medium low. Sautee with occasional stirring until the carrots are nearly done, about 8 minutes. Add the myceliated rice, myceliated grain and or myceliated seed, and stir. Cook for another two minutes then add the spinach. You may have to break up the chunks if still frozen. Frozen spinach is much better than fresh spinach for curries. Add coconut milk and lemon juice, stir, then bring to a low simmer for a few minutes, until the spinach begins to cook. Turn off the heat and enjoy Myceliated Spinach Curry.

Extraction Example

Substrate(s) not utilized in tempeh-form as functional food(s) are formulated into nutraceuticals by extraction using water, heat, mechanical agitation, filtration and then modified by formulated association with small molecules as follows: 100 g to 1000 g of myceliated-substrate is extracted in 4 L to 10 L of boiling water with 1 g to 100 g citric acid and 1 g to 100 g ascorbic acid, for 1 h to 4 hours, filtered through a fine stainless steel colander discarding solid substrate, with the liquid then being concentrated to ½ to ⅛ original volume by boiling and stirring. To every 40 ml to 60 ml of hot liquid extract, mostly polysaccharides, is added 1 ml to 20 ml citrus essential oils of orange, lemon, lime, grapefruit, tangerine and combinations thereof, and 100 g to 200 g dry honey, with vigorous stirring, at 145 degrees F. to 165 degrees F. for 10 min to 45 min, then cooled to 100 degrees F. to 125 degrees F. Dry honey in this invention means bee honey whose physical state is somewhat more solid than liquid at room temperature.

Decanting Products

In decanting product(s), honey formulations are stirred for 10 min to 90 min at 100 degrees F. to 125 degrees F., then poured into small glass bottles and sold as a variety of products including: "Reishi Honey", "Lions Mane Honey", "Cordyceps Honey", "Shiitake Honey", "Maitake Honey", "Turkey-Tail Honey", "Enokitake Honey", "Oyster Mushroom Honey", "Reishi-Cordyceps Honey", "Reishi Coffee", "Reishi Coffee Honey", "Reishi Chocolate", "Reishi Chocolate Honey", "Reishi Vanilla", "Reishi Vanilla Honey", etc. Myceliated substrate is also reformulated into value-added products including "Lions Mane Egg Noodles", "Reishi Egg Noodles", "Shiitake Egg Noodles", etc., for use in a wide variety of value-added, biologically-active, nutraceutical and functional food form(s), which are then traditionally cooked and consumed in order to enjoy the nutraceutical and functional food benefits of this invention.

This invention also includes a method for using *Tremella fuciformis, Pholiota nameko, Flammulina velutipes*, and or *Ganoderma lucidum* to myceliate raw flax seed and or chia seed such that when prepared, fermented, and formulated as disclosed, produces extraordinarily slippery jelly which when filtered and purified has commercial, home and clinical application including phenomena such as enhancing digestion or lubrication of mucus membranes.

Further Examples

Extracts of fungi used herein are known to be of low glycemic index which adds health-care benefits to the honey formulations. Interestingly, this low-glycemic effect is enhanced by manipulating the honey formulations into pills and or capsules, which take longer to metabolize than the honey formulations by themselves, by dilution at 100 degrees F. to 145 degrees F. of 1 part honey formulations into 2 to 10 parts purified cellulose powder and or 2 into 10 parts raw mushroom powder (w/w), as filler, mixing, then pressing mix into molds at 20 lb/in2 to 200 lb/in2 pressure at 70 degrees F. to 100 degrees F. to make pills and or capsules which are then consumed in order to enjoy the related health-care benefits of this invention. Similarly, suppositories, which also take longer to metabolize than honey formulations themselves, are made as follows: take 1 part to 10 parts Honey and dilute into 10 to 1000 parts coconut butter modified with 1 to 10 parts olive oil, to ensure softness, and heat mixture from 145 degrees F. to 175 degrees F., after vigorous mixing, formulation is brought back to room temperature to cool, once cooled, formulation into 1 in to 2 in long cylinders of ½ in diameter and packaged.

In another embodiment: continuous, large batch liquid-state and solid-state operation; pure cultures are grown aerobically and inoculated into large industrial liquid-state and large solid-state commercial processors operated continuously and semi-anaerobically for large-scale fermentation of food product(s). After cultures of media turn completely white or the representative color thereof for that particular species, and have completely overgrown and commanded the medium and are resistant to gentle mixing, the contents are harvested, removed to plastic bags and refrigerated for quick use at either 40 degrees F., or frozen for long-term storage, and subsequent utilization, at minus 20 degrees F. Fermented media are prepared into gourmet human foods including: "tempeh style" meat substitutes, egg-noodles, specialty flavorings, breads, extracts and cooking-sauces, or used directly as a fresh ingredient in soup an or stir fry recipes; or packaged for delivery and sales. Nutriceuticals are produced as above but large-scale, utilizing large, continuous methods of agitated liquid-state and solid-state fermentation.

List of Various Agricultural Substrates

This invention pertains to methods of liquid-state and solid-state myceliation of agricultural substrates into a range of potent nutraceuticals and delicious functional foods for humans. Agricultural substrates that may be myceliated in accordance with this invention include: all cereals, grains, all species of wheat, rye, brown rice, white rice, red rice, gold rice, wild rice, rice, barley, triticale, rice, sorghum, oats, millets, quinoa, buckwheat, fonio, amaranth, teff and durum; apples and pears, apricots, cherries, almonds, peaches, strawberries, raisins, manioc, cacao, banana, Rubiaceae spp. (coffee), lemons, oranges and grapefruit; tomatoes, potatoes, peppers, eggplant, Allspice, mango powder, Angelica, Anise (*Pimpinella anisum*), Aniseed myrtle (*Syzygium anisatum*), Annatto (*Bixa orellana*), Apple mint (*Mentha suaveolens*), *Artemisia vulgaris*, Mugwort, Asafoetida (*Ferula assafoetida*), Berberis, Banana, Basil (*Ocimum basilicum*), Bay leaves, Bistort (*Persicaria bistorta*), Black cardamom, Black cumin, Blackcurrant, Black limes, Bladder wrack (*Fucus vesiculosus*), Blue Cohosh, Blue-leaved Mallee (*Eucalyptus polybractea*), Bog Labrador Tea (*Rhododendron groenlandicum*), Boldo (*Peumus boldus*), Bolivian Coriander (*Porophyllum ruderale*), Borage (*Borago officinalis*), Calamus, Calendula, Calumba (*Jateorhiza calumba*), Chamomile, Caper (*Capparis spinosa*), Caraway, Cardamom, Carob Pod, Cassia, Casuarina, Catnip, Cat's Claw, Catsear, Cayenne pepper, *Celastrus paniculatus*, Comfrey, Celery salt, Celery seed, Centaury, Chervil (*Anthriscus cerefolium*), Chickweed, Chicory, Chile pepper, Chili powder, Cinchona, Chives (*Allium schoenoprasum*), Cicely (*Myrrhis odorata*), Cilantro (see Coriander) (*Coriandrum sativum*), Cinnamon (and *Cassia*), Cinnamon Myrtle (*Backhousia myrtifolia*), Clary, Cleavers, Clover, Cloves, Coltsfoot, Comfrey, Common Rue, Condurango, Coptis, Coriander, Costmary (*Tanacetum balsamita*), Couchgrass, Cow Parsley (*Anthriscus sylvestris*), Cowslip, Cramp Bark (*Viburnum opulus*), Cress, Cuban Oregano (*Plectranthus amboinicus*), Cudweed, Cumin, Curry leaf (*Murraya koenigii*), Damiana (*Turnera aphrodisiaca*), Dandelion (*Taraxacum officinale*), Demulcent, Devil's claw (*Harpagophytum procumbens*), Dill seed, Dill (*Anethum graveolens*), Dorrigo Pepper (*Tasmannia stipitata*), Echinacea, Echinopanax Elatum, Edelweiss, Elderberry, Elderflower, Elecampane, *Eleutherococcus senticosus*, Epazote (*Chenopodium ambrosioides*), Ephedra, *Eryngium foetidum*, Eucalyptus, Fennel (*Foeniculum vulgare*), Fenugreek, Feverfew, Figwort, Five-spice powder (Chinese), Fo-ti-tieng, Fumitory, Galangal, Garam masala, Garden cress, Garlic chives, Garlic, Ginger (*Zingiber officinale*), Ginkgo biloba, Ginseng, Siberian (*Eleutherococcus senticosus*), Goat's Rue (*Galega officinalis*), Goada masala, Golden Rod, Golden Seal, Gotu Kola, Grains of paradise (*Aframomum melegueta*), Grains of Selim (*Xylopia aethiopica*), Grape seed extract, Green tea, Ground Ivy, Guaco, Gypsywort, Hawthorn (*Crataegus sanguinea*), Hawthorne Tree, Hemp, Herbes de Provence, Hibiscus, Holly, Holy Thistle, Hops, Horehound, Horseradish, Horsetail (*Equisetum telmateia*), Hyssop (*Hyssopus officinalis*), Jalap, Jasmine, Jiaogulan (*Gynostemma pentaphyllum*), Joe Pye weed (Gravelroot), John the Conqueror, Juniper, Kaffir Lime Leaves (*Citrus hystrix, C. papedia*), Kaala masala, Knotweed, Kokam, Labrador tea, Lady's Bedstraw, Lady's Mantle, Land cress, Lavender (*Lavandula* spp.), Ledum, Lemon Balm (*Melissa officinalis*), Lemon basil, Lemongrass (*Cymbopogon citratus, C. flexuosus*, and other species), Lemon Ironbark (*Eucalyptus staigeriana*), Lemon mint, Lemon Myrtle (*Backhousia citriodora*), Lemon Thyme, Lemon verbena (*Lippia citriodora*), Licorice-adaptogen, Lime Flower, *Limnophila aromatica*, Lingzhi, Linseed, Liquorice, Long pepper, Lovage (*Levisticum officinale*), Luohanguo, Mace, Mahlab, Malabathrum, Manchurian Thorn Tree (*Aralia manchurica*), Mandrake, Marjoram (*Origanum majorana*), Marrubium vulgare, Marsh Labrador Tea, Marshmallow, Mastic, Meadowsweet, Mei Yen, Melegueta pepper (*Aframomum melegueta*), Mint, Milk thistle (*Silybum*), Bergamot (*Monarda didyma*), Motherwort, Mountain Skullcap, Mullein (*Verbascum thapsus*), Mustard, Mustard seed, *Nashia inaguensis*, Neem, Nepeta, Nettle, *Nigella sativa*, Kolanji, Black caraway, Noni, Nutmeg, Mace, Marijuana, *Oenothera* (*Oenothera biennis*), Olida (*Eucalyptus olida*), Oregano (*Origanum vulgare, O. heracleoticum*), Orris root, Osmorhiza, Olive Leaf (used in tea and as herbal supplement), *Panax quinquefolius*, Pandan leaf, Paprika, Parsley (*Petroselinum crispum*), Passion Flower, Patchouli, Pennyroyal, Pepper (black, white, and green), Peppermint, Peppermint Gum (*Eucalyptus dives*), Perilla, Plantain, Pomegranate, Ponch phoran, Poppy seed, Primrose (*Primula*), candied flowers, dry tea mixes, Psyllium, Purslane, Quassia, Quatre epices, Ramsons, Raspberry (leaves), Reishi, Restharrow, Rhodiola rosea, Riberry (*Syzygium luehmannii*), Rocket/Arugula, Roman chamomile, Rooibos, Rosehips, Rosemary (*Rosmarinus officinalis*), Rowan Berries, Rue, Safflower, Saffron, Sage (*Salvia officinalis*), Saigon Cinnamon, St John's Wort, Salad Burnet (*Sanguisorba minor* or *Poterium sanguisorba*), *Salvia*, Sichuan Pepper (Sansho), *Sassafras*, Savory (*Satureja hortensis, S. montana*), *Schisandra* (*Schisandra chinensis*), *Scutellaria costaricana*, Senna (herb), *Senna obtusifolia*, Sesame seed, Sheep Sorrel, Shepherd's Purse, Sialagogue, Siberian Chaga, Siberian ginseng (*Eleutherococcus senticosus*), *Siraitia grosvenorii* (luohanguo), Skullcap, Sloe Berries, Smudge Stick, *Sonchus*, Sorrel (*Rumex* spp.), Southernwood, Spearmint, Speedwell, Squill, Star anise, *Stevia*, Strawberry Leaves, Suma (*Pfaffia paniculata*), Sumac, Summer savory, *Sutherlandia frutescens*, Sweet grass, Sweet cicely (*Myrrhis odorata*), Sweet woodruff, Szechuan pepper (*Xanthoxylum piperitum*), Tacamahac, Tamarind, Tandoori masala, Tansy, Tarragon (*Artemisia dracunculus*), Tea, Teucrium polium, That basil, Thistle, Thyme, Toor Dall, Tormentil, *Tribulus terrestris*, Tulsi (*Ocimum tenuiflorum*), Turmeric (*Curcuma longa*), Uva Ursi also known as Bearberry, Vanilla (*Vanilla planifolia*), Vasaka, Vervain, Vetiver, Vietnamese Coriander (*Persicaria odorata*), Wasabi (*Wasabia japonica*), Watercress, Wattleseed, Wild ginger, Wild Lettuce, Wild thyme, Winter savory, Witch Hazel, Wolfberry, Wood Avens, Wood Betony, Woodruff, Wormwood, Yarrow, Yerba Buena, Yohimbe, Za'atar, Zedoary Root, or derivations thereof in aqueous or semi-aqueous solution(s).

We claim:

1. A method for myceliating coffee beans, comprising:
sterilizing the coffee beans under pressure;
providing a submerged fungal liquid tissue culture grown in a media consisting of a fruit-based and vegetable-based liquid-state media in the absence of an additional nitrogen source;
inoculating the sterilized coffee beans with the submerged fungal liquid tissue culture; and
enabling the fungal culture to incubate the fungal mycelium on the coffee beans to prepare the myceliated coffee beans, wherein the myceliated coffee beans are capable of being used to prepare a palatable coffee beverage for human consumption.

2. A method as set forth in claim 1 further comprising: preparing the fungal liquid tissue culture by harvesting a floating mass of hyphae derived from unagitated liquid state fermentation, and inoculating the coffee beans with the hyphae.

3. The method of claim 1, wherein the step of
enabling the fungal culture to grow fungal mycelium on the coffee beans wherein the coffee beans are infused with fungal metabolites.

4. A method as set forth in claim 3, wherein the step of enabling infuses the coffee beans with β glucans.

5. A method as set forth in claim 3, wherein the step of enabling infuses the coffee beans with LZ-8 protein.

6. A method as set forth in claim 3, wherein the step of enabling infuses the coffee beans with ganoderic acids.

7. A method as set forth in claim 3, wherein the step of enabling infuses the coffee beans with lucidenic acids.

8. The method of claim 3, wherein the step of
enabling the fungal culture to grow fungal mycelium on the coffee beans wherein the coffee beans are infused with a component selected from the group consisting of: polysaccharides, proteins, glycoproteins, nucleic acids, ergosterol, and erinacines.

9. A method for myceliating coffee beans as set forth in claim 1, wherein the method further comprises roasting the harvested coffee beans.

10. The method of claim 1, wherein the liquid fungal tissue culture is comprised of fungi selected from the group consisting of *A. blazei, C. sinensis, G. lucidum, H. erinaceus, G. frondosa, P. eryngii, P. ostreatus, P. citrinopileatus, P. djamor, T. versicolor, L. edodes, F. velutipes, V. volvacea, H. marmoreus, P. nameko, M. hortensis, M. angusticeps, P. umbellatus,* and *T. fuciformis.*

11. The method of claim 10, wherein the liquid fungal tissue culture is comprised of fungi selected from the group consisting of *C. sinensis, G. lucidum T. versicolor, T. fuciformis, G. frondosa,* and *P. nameko.*

* * * * *